United States Patent
Olson et al.

(10) Patent No.: US 12,036,027 B2
(45) Date of Patent: *Jul. 16, 2024

(54) FLEXIBLE HIGH-DENSITY MAPPING CATHETER

(71) Applicant: St. Jude Medical, Cardiology Division, Inc., St. Paul, MN (US)

(72) Inventors: Gregory K. Olson, Elk River, MN (US); Don Curtis Deno, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 342 days.

This patent is subject to a terminal disclaimer.

(21) Appl. No.: 17/501,982

(22) Filed: Oct. 14, 2021

(65) Prior Publication Data

US 2022/0061727 A1  Mar. 3, 2022

Related U.S. Application Data

(63) Continuation of application No. 15/793,093, filed on Oct. 25, 2017, now Pat. No. 11,172,858.
(Continued)

(51) Int. Cl.
*A61B 5/287* (2021.01)
*A61B 5/00* (2006.01)
(Continued)

(52) U.S. Cl.
CPC ............ *A61B 5/287* (2021.01); *A61B 5/6858* (2013.01); *A61B 18/1492* (2013.01);
(Continued)

(58) Field of Classification Search
CPC ..... A61B 5/287; A61B 5/6852; A61B 5/6859; A61B 5/6869; A61B 2018/00351;
(Continued)

(56) References Cited

U.S. PATENT DOCUMENTS 4,522,212 A  6/1985  Gelinas et al.
5,224,939 A  7/1993  Holman et al.
(Continued)

FOREIGN PATENT DOCUMENTS

AU  2015202258 A1  5/2015
AU  2015202258 B2  6/2016
(Continued)

OTHER PUBLICATIONS

Haldar et al., "Omnipolar Voltage Amplitude Correlates to Largest Measurable Bipolar Vpp", Circulation: Arrhythmia and Electrophysiology, Sep. 2017, pp. 6.
(Continued)

*Primary Examiner* — Eun Hwa Kim
(74) *Attorney, Agent, or Firm* — Kilpatrick Townsend & Stockton LLP

(57) ABSTRACT

Aspects of the present disclosure are directed to flexible high-density mapping catheters with a planar array of high-density mapping electrodes near a distal tip portion. These mapping catheters may be used to detect electrophysiological characteristics of tissue in contact with the electrodes, and may be used to diagnose cardiac conditions, such as cardiac arrhythmias for example.

15 Claims, 9 Drawing Sheets
(5 of 9 Drawing Sheet(s) Filed in Color)

Related U.S. Application Data

(60) Provisional application No. 62/414,634, filed on Oct. 28, 2016.

(51) Int. Cl.
 *A61B 18/14* (2006.01)
 *A61B 34/00* (2016.01)
 *A61B 34/20* (2016.01)
 *A61B 18/00* (2006.01)

(52) U.S. Cl.
 CPC .............. *A61B 34/20* (2016.02); *A61B 34/25* (2016.02); *A61B 2018/00351* (2013.01); *A61B 2018/00357* (2013.01); *A61B 2018/00363* (2013.01); *A61B 2018/00577* (2013.01); *A61B 2018/00839* (2013.01); *A61B 2018/1465* (2013.01); *A61B 2034/2051* (2016.02)

(58) Field of Classification Search
 CPC .......... A61B 2018/00357; A61B 2018/00839; A61B 18/1492
 See application file for complete search history.

(56) References Cited

U.S. PATENT DOCUMENTS

| | | |
|---|---|---|
| 5,380,301 A | 1/1995 | Prichard et al. |
| 5,400,783 A | 3/1995 | Pomeranz et al. |
| 5,456,254 A | 10/1995 | Pietroski et al. |
| 5,626,136 A | 5/1997 | Webster, Jr. |
| 5,702,438 A | 12/1997 | Avitall |
| 5,715,817 A | 2/1998 | Stevens-Wright et al. |
| 5,715,832 A | 2/1998 | Koblish et al. |
| 5,827,278 A | 10/1998 | Webster, Jr. |
| 5,876,373 A | 3/1999 | Giba et al. |
| 5,964,757 A | 10/1999 | Ponzi |
| 6,029,091 A | 2/2000 | de la Rama et al. |
| 6,071,282 A | 6/2000 | Fleischman |
| 6,074,379 A | 6/2000 | Prichard |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,273,404 B1 | 8/2001 | Holman et al. |
| 6,415,187 B1 | 7/2002 | Kuzma et al. |
| 6,491,681 B1 | 12/2002 | Kunis et al. |
| 6,522,932 B1 | 2/2003 | Kuzma et al. |
| 6,554,794 B1 | 4/2003 | Mueller et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,004,937 B2 | 2/2006 | Lentz et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,214,220 B2 | 5/2007 | McGlinch et al. |
| 7,217,256 B2 | 5/2007 | Di Palma |
| 7,228,164 B2 | 6/2007 | Fuimaono et al. |
| 7,257,435 B2 | 8/2007 | Plaza |
| 7,412,274 B2 | 8/2008 | Mejia |
| 7,429,261 B2 | 9/2008 | Kunis et al. |
| 7,561,907 B2 | 7/2009 | Fuimaono et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,157,848 B2 | 4/2012 | Zhang et al. |
| 8,187,267 B2 | 5/2012 | Pappone et al. |
| 8,206,404 B2 | 6/2012 | de la Rama et al. |
| 8,221,390 B2 | 7/2012 | Pal et al. |
| 8,271,099 B1 | 9/2012 | Swanson |
| 8,273,016 B2 | 9/2012 | O'Sullivan |
| 8,376,990 B2 | 2/2013 | Ponzi et al. |
| 8,391,947 B2 | 3/2013 | Urman et al. |
| 8,447,377 B2 | 5/2013 | Harlev et al. |
| 8,486,063 B2 | 7/2013 | Werneth et al. |
| 8,565,894 B2 | 10/2013 | Vetter et al. |
| 8,603,069 B2 | 12/2013 | Selkee |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,744,599 B2 | 6/2014 | Tegg |
| 8,755,861 B2 | 6/2014 | Harlev et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,044,245 B2 | 6/2015 | Condie et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,486,280 B2 | 11/2016 | Koblish et al. |
| 9,486,282 B2 | 11/2016 | Solis |
| 9,532,703 B2 | 1/2017 | Huszar et al. |
| 9,539,413 B2 | 1/2017 | Ogle |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,713,418 B2 | 7/2017 | Huszar et al. |
| 9,788,895 B2 | 10/2017 | Solis |
| 9,820,664 B2 | 11/2017 | Hoitink et al. |
| 9,833,608 B2 | 12/2017 | Masson |
| 9,844,645 B2 | 12/2017 | Pai et al. |
| 9,848,795 B2 | 12/2017 | Marecki et al. |
| 9,907,480 B2 | 3/2018 | Basu et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,143,394 B2 | 12/2018 | Solis |
| 10,285,610 B2 | 5/2019 | Wu |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |

(56) References Cited

U.S. PATENT DOCUMENTS

| | | |
|---|---|---|
| 10,702,177 B2 | 7/2020 | Aujla |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,953,196 B2 | 3/2021 | Raab et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,141,568 B2 | 10/2021 | Hsueh et al. |
| 11,160,482 B2 | 11/2021 | Solis |
| 11,272,886 B2 | 3/2022 | Harlev et al. |
| 2002/0165484 A1 | 11/2002 | Bowe et al. |
| 2005/0159741 A1 | 7/2005 | Paul et al. |
| 2009/0198300 A1 | 8/2009 | Zhang et al. |
| 2010/0152731 A1 | 6/2010 | de la Rama et al. |
| 2010/0174177 A1 | 7/2010 | Wu |
| 2010/0286684 A1 | 11/2010 | Hata et al. |
| 2011/0118582 A1 | 5/2011 | De la Rama et al. |
| 2011/0118726 A1 | 5/2011 | de la Rama et al. |
| 2011/0288392 A1 | 11/2011 | de la Rama et al. |
| 2012/0010490 A1 | 1/2012 | Kauphusman et al. |
| 2012/0271302 A1 | 10/2012 | Behl et al. |
| 2012/0296232 A1 | 11/2012 | Ng |
| 2013/0085479 A1 | 4/2013 | de la Rama et al. |
| 2013/0253504 A1 | 9/2013 | Fang |
| 2013/0274582 A1 | 10/2013 | Afonso et al. |
| 2014/0100639 A1 | 4/2014 | Lee et al. |
| 2014/0200639 A1 | 7/2014 | de la Rama |
| 2014/0269602 A1 | 9/2014 | Kawagishi |
| 2014/0296846 A1 | 10/2014 | Huszar et al. |
| 2014/0296902 A1 | 10/2014 | Huszar et al. |
| 2014/0316496 A1 | 10/2014 | Masson et al. |
| 2014/0336636 A1 | 11/2014 | Huszar et al. |
| 2014/0350564 A1 | 11/2014 | Huszar et al. |
| 2015/0105645 A1 | 4/2015 | Subramaniam et al. |
| 2015/0119911 A1 | 4/2015 | Mckenzie |
| 2015/0141785 A1 | 5/2015 | Hayam et al. |
| 2015/0159741 A1 | 6/2015 | Versteyhe et al. |
| 2015/0351652 A1 | 12/2015 | Marecki et al. |
| 2016/0143588 A1 | 5/2016 | Hoitink et al. |
| 2016/0213423 A1 | 7/2016 | Kauphusman et al. |
| 2016/0213916 A1 | 7/2016 | de la Rama |
| 2016/0278851 A1 | 9/2016 | Mannion et al. |
| 2016/0317094 A1 | 11/2016 | Byrd et al. |
| 2016/0331471 A1 | 11/2016 | Deno et al. |
| 2016/0331933 A1 | 11/2016 | Knutsen |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | de la Rama et al. |
| 2017/0112405 A1 | 4/2017 | Sterrett et al. |
| 2017/0273738 A1 | 9/2017 | Wu |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0050190 A1 | 2/2018 | Masson |
| 2018/0056038 A1 | 3/2018 | Aujla |
| 2018/0070845 A1 | 3/2018 | Hoitink et al. |
| 2018/0085064 A1 | 3/2018 | Auerbach et al. |
| 2018/0235496 A1 | 8/2018 | Wu et al. |
| 2018/0303361 A1 | 10/2018 | Wu et al. |
| 2019/0175043 A1 | 6/2019 | Wu et al. |
| 2019/0192826 A1 | 6/2019 | Wada |
| 2020/0077912 A1 | 3/2020 | Wu et al. |
| 2020/0138378 A1 | 5/2020 | de La Rama et al. |
| 2020/0155021 A1 | 5/2020 | Wu et al. |
| 2020/0221966 A1 | 7/2020 | Wu et al. |
| 2020/0229727 A1 | 7/2020 | Hoitink et al. |
| 2020/0253496 A1 | 8/2020 | Deno et al. |
| 2020/0329989 A1 | 10/2020 | Aujla |
| 2020/0405166 A1 | 12/2020 | Wu et al. |
| 2021/0145342 A1 | 5/2021 | Wang |
| 2021/0187246 A1 | 6/2021 | Houck |
| 2021/0204871 A1 | 7/2021 | Goedeke et al. |
| 2021/0228137 A1 | 7/2021 | Aujla |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |

FOREIGN PATENT DOCUMENTS

| | | |
|---|---|---|
| AU | 2016204351 A1 | 1/2017 |
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101797181 A | 8/2010 |
| CN | 101927053 B | 1/2015 |
| CN | 103157168 B | 4/2015 |
| CN | 101797181 B | 12/2015 |
| CN | 105960201 A | 9/2016 |
| CN | 106264715 A | 1/2017 |
| CN | 106264716 A | 1/2017 |
| CN | 106308790 A | 1/2017 |
| CN | 106859765 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 111657866 A | 9/2020 |
| CN | 106264715 B | 11/2020 |
| CN | 106264716 B | 11/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |
| EP | 2732843 A1 | 5/2014 |
| EP | 2747680 A2 | 7/2014 |
| EP | 2752153 A1 | 7/2014 |
| EP | 2907462 A1 | 8/2015 |
| EP | 2915555 A1 | 9/2015 |
| EP | 2732843 B1 | 1/2016 |
| EP | 1968679 B1 | 9/2016 |
| EP | 2241279 B1 | 9/2016 |
| EP | 3114987 A1 | 1/2017 |
| EP | 2796103 B1 | 2/2017 |
| EP | 3222209 A1 | 9/2017 |
| EP | 2792322 B1 | 10/2017 |
| EP | 2792323 B1 | 10/2017 |
| EP | 3115076 A4 | 10/2017 |

(56) References Cited

FOREIGN PATENT DOCUMENTS

| | | |
|---|---|---|
| EP | 3117863 A4 | 10/2017 |
| EP | 3287092 A1 | 2/2018 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3363397 A1 | 8/2018 |
| EP | 2907462 B1 | 9/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3434218 B1 | 2/2020 |
| EP | 2908723 B1 | 3/2020 |
| EP | 3114987 B1 | 8/2020 |
| EP | 3178516 B1 | 9/2020 |
| EP | 3738508 A1 | 11/2020 |
| EP | 3738509 A1 | 11/2020 |
| EP | 3340916 B1 | 12/2020 |
| EP | 3750475 A1 | 12/2020 |
| EP | 2155301 B1 | 4/2021 |
| EP | 3432820 B1 | 4/2021 |
| EP | 2809254 B1 | 6/2021 |
| EP | 3508245 B1 | 7/2021 |
| EP | 3858277 A1 | 8/2021 |
| EP | 3791820 B9 | 4/2022 |
| IL | 246415 B | 12/2019 |
| IN | 201614021431 A | 12/2016 |
| IN | 201614021432 A | 12/2016 |
| IN | 201614021450 A | 12/2016 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 2017012750 A | 1/2017 |
| JP | 2017012755 A | 1/2017 |
| JP | 2017038919 A | 2/2017 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 4/2019 |
| JP | 6528010 B1 | 5/2019 |
| JP | 6655655 B2 | 2/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 6843502 B2 | 3/2021 |
| JP | 6920312 B2 | 8/2021 |
| JP | 6926306 B2 | 8/2021 |
| JP | 6932484 B2 | 8/2021 |
| JP | 6980386 B2 | 11/2021 |
| JP | 2022020838 A | 2/2022 |
| RU | 2016124794 A | 12/2017 |
| RU | 2016124801 A | 12/2017 |
| RU | 2016125763 A | 1/2018 |
| WO | 9843530 A1 | 10/1998 |
| WO | 0168178 A1 | 9/2001 |
| WO | 2008091197 A1 | 7/2008 |
| WO | 2011159861 A2 | 12/2011 |
| WO | 2011159955 A1 | 12/2011 |
| WO | 2014113612 A1 | 7/2014 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |
| WO | 2017098198 A1 | 6/2017 |
| WO | 2018053148 A1 | 3/2018 |
| WO | 2018053164 A1 | 3/2018 |

OTHER PUBLICATIONS

Magtibay et al., "Omnipoles Provide the Largest Possible Bipolar Voltages", Journal of the American Heart Association, 2017, pp. 6-7.

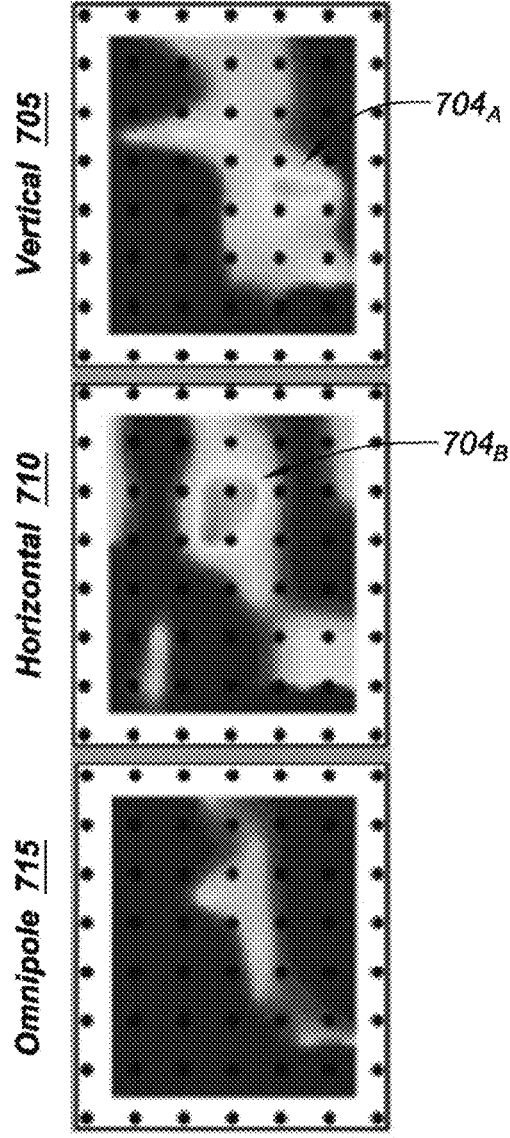
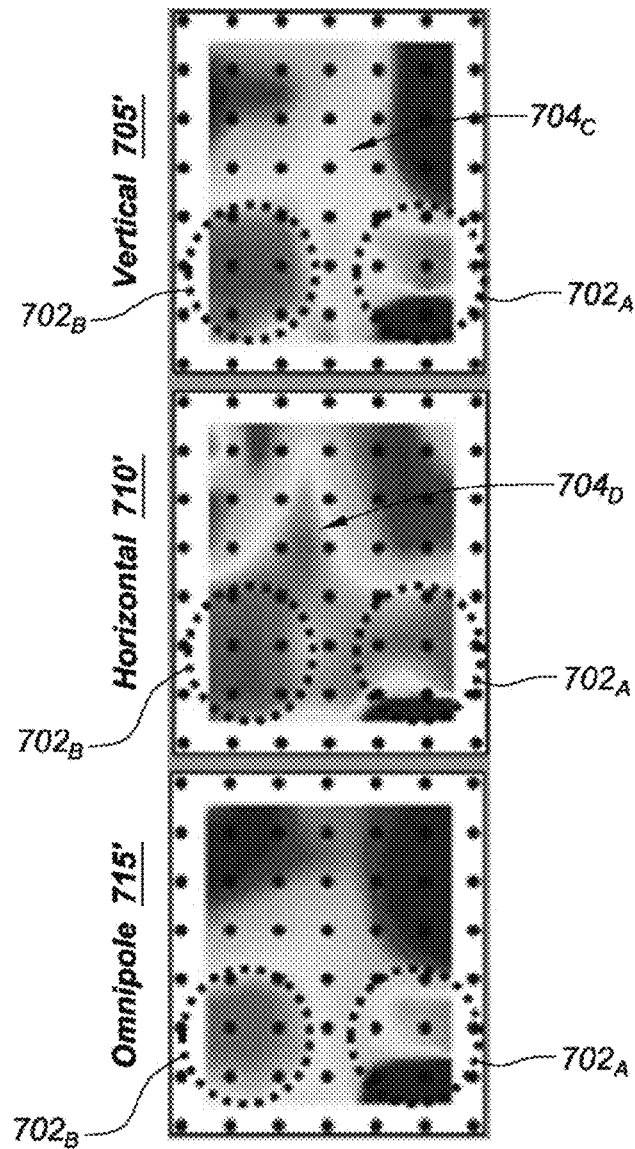
FIG. 7A           FIG. 7B

FLEXIBLE HIGH-DENSITY MAPPING CATHETER

CROSS-REFERENCE TO RELATED APPLICATIONS

The present application is a continuation of application Ser. No. 15/793,093, filed 25 May 2017, now U.S. Pat. No. 11,172,858, which claims priority to U.S. provisional application No. 62/414,634, filed 28 Oct. 2016, which is are hereby incorporated by reference as though fully set forth herein.

BACKGROUND a. Field

The instant disclosure relates to high-density mapping catheters for diagnosing, for example, cardiac arrhythmias. In particular, the instant disclosure relates to flexible planar arrays including a plurality of electrodes positioned in a high-density array.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring, electrodes. It can be difficult to maintain good electrical contact with cardiac tissue when using these conventional catheters and their relatively rigid (or nonconforming), metallic electrodes, especially when sharp gradients and undulations are present.

When mapping a cardiac muscle, the beating of the heart, especially if erratic or irregular, makes it difficult to keep adequate contact between electrodes and tissue for a sufficient length of time. These problems are exacerbated on contoured, irregular, or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

The instant disclosure relates to high-density mapping catheter tips for diagnosing, for example, cardiac arrhythmias. In particular, the instant disclosure relates to catheters with a planar array coupled to a distal end of a catheter shaft. The planar array includes a plurality of electrodes aligned in a high-density array to facilitate high-resolution electrophysiology mapping of tissue in contact with the plurality of electrodes.

Various embodiments of the present disclosure are directed to a planar array catheter including an elongated catheter shaft and a flexible, planar array. The elongated catheter shaft includes a proximal end and a distal end, and defines a catheter longitudinal axis extending between the proximal and distal ends. The flexible, planar array is coupled to the distal end of the catheter shaft, and includes two or more arms extending substantially parallel with the longitudinal axis and laying in a plane. Each of the arms conforms to tissue and includes a plurality of electrodes mounted thereon. The plurality of electrodes are equally spaced along both a length of each arm and across adjacent arms. In some specific embodiments, the plurality of electrodes may sample electrical characteristics of contacted tissue in at least two substantially transverse directions.

Some aspects of the present disclosure are directed to an electrophysiology mapping system including a planar array catheter and controller circuitry. The planar array catheter includes a catheter shaft, and a flexible, planar array coupled to a distal end of the catheter shaft. The planar array conforms to tissue, and includes two or more arms extending substantially parallel with the longitudinal axis and laying in a plane. Each of the arms have a plurality of electrodes mounted thereon with equal spacing along a length of each arm and across adjacent arms. The controller circuitry is communicatively coupled to each of the plurality of electrodes, and samples electrical signals received from each of the plurality of electrodes. In specific embodiments, the plurality of electrodes sample electrical characteristics of the contacted tissue, and the controller circuitry processes the sampled electrical characteristics of the contacted tissue through an OIS/OT algorithm. The controller circuitry may produce an output indicative of the true electrical characteristics of the contacted tissue, independent of the orientation of the planar array catheter relative to the contacted tissue.

The foregoing and other aspects, features, details, utilities, and advantages of the present disclosure will be apparent from reading the following description and claims, and from reviewing the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various example embodiments may be more completely understood in consideration of the following detailed description in connection with the accompanying drawings, in which:

FIG. 7A depicts the vertical, horizontal, and omnipole electrophysiology maps based on the electrical data collected from the planar array of FIG. 7 before ablation of the contacted tissue, consistent with various embodiments of the present disclosure.

FIG. 7B depicts the vertical, horizontal, and omnipole electrophysiology maps based on the electrical data collected from the planar array of FIG. 7 after ablation of the contacted tissue, consistent with various embodiments of the present disclosure.

Figure 1A:
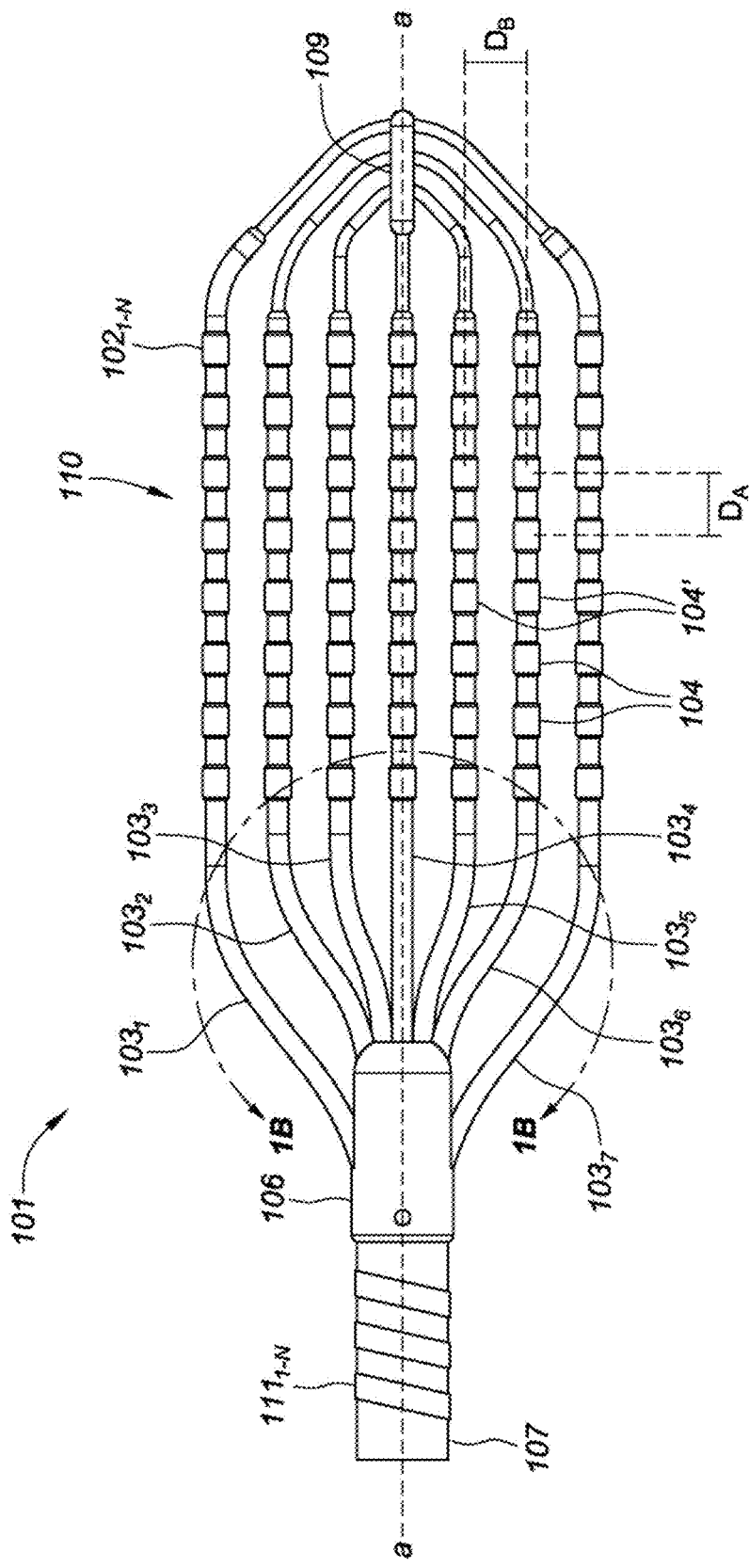
FIG. 1A is a plan view of a planar array of an electrophysiology catheter, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Various embodiments of the present disclosure are directed to flexible, high-density mapping catheters. In general, the tip portions of these high-density mapping catheters comprise an underlying support framework that is adapted to conform to and remain in contact with tissue (e.g., a beating heart wall).

Aspects of the present disclosure are directed toward planar array catheters with substantially uniform spacing, and/or known and constant spacing, between electrodes which form bipole pairs for electrophysiology mapping. More advanced embodiments of the present disclosure may utilize orientation independent sensing/omnipolar technology ("OIS/OT") and related algorithms to mitigate the need for substantially square electrode arrays. OIS/OT and related algorithms are discussed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, which are hereby incorporated by referenced as though fully disclosed herein.

While some electrophysiology mapping catheters may consist of equally spaced electrodes along a length of a planar array arm, the present disclosure is directed toward planar arrays with equal spacing of electrodes along both a length of the arms of the array, as well as between arms (i.e., x and y directions).

In some specific aspects of the present disclosure a planar array catheter including 7 arms is disclosed. Each of the arms may be aligned with, and extend parallel to, a longitudinal axis of the catheter shaft. Each arm is coupled to the other arms of the planar array at proximal and distal ends.

The arms each include a row of electrodes extending along a length of the arm. The electrodes are evenly distributed along the length of the arm and between adjacent arms of the planar array.

Uniform spacing between adjacent electrodes in an array (in two or more directions) facilitates simplified and robust OIS/OT-like assessments of orientation-specific electrical characteristics of myocardial tissue, for example. In some embodiments, orthogonal and identical spacing directly permits 2-directional assessments of electrical activation direction and maximum voltage amplitude of sampled tissue. Moreover, uniform electrode spacing allows for the use of diagonal bipole pairs which are orthogonal. (relative to one another), and substantially measure the electrical characteristics of the same tissue area. The variation in readings between the orthogonal bipole pairs may be attributed to orientation-specific electrical characteristics of the contacted tissue. Embodiments of the present disclosure may further facilitate reduced complexity decimation by skipping intermediate electrodes, and forming bipole pairs with larger electrode spacing configurations than created by adjacent electrodes in the array. Decimation may be used to determine electrical characteristics of tissue at a less granular resolution. Further, a clinician may assess situational performance of the planar array at various bipole spacings. In various embodiments consistent with the present disclosure, adjacent bipole pairs may have various spacings, and be oriented in such a way as to facilitate various spatial orientations relative to one another.

The benefits of equal electrode spacing along two or more perpendicular directions include an effective and simplified compensation scheme for signals received from a clique (group) of electrodes, and six degrees of freedom ("DOF") orientation and position information in an impedance-based navigation system's coordinate frame (e.g., the NavX™ navigation system manufactured by St. Jude Medical, Inc.). The six DOF orientation and position information may be based on the determined position of the electrodes within the patient's body. A simplified computation of the electric field vector for cliques may be determined based only on average bipole voltages in the x, y (and possibly z) directions. Equal electrode spacing may also facilitate OIS/OT-like methods that generate bipolar electrogram signals at various orientations with respect to wavefronts so that a clinician may employ arbitrary catheter orientations. Finally, the equal electrode spacing of the array facilitates a balanced and integrated view of voltage, fractionation, and/or activation patterns, which may be readily sampled from adjacent electrodes with known/equal spacing. This information may then be used to compute a divergence and curl (i.e., to detect/locate foci and rotor cores from activation directions).

In some specific embodiments of an electrophysiology planar array catheter in accordance with the present disclosure, the planar array may include 7 arms, each arm having 8 electrodes extending along a length of the arm with 2 millimeter ("mm") spacing. The spacing between electrodes of adjacent arms also being 2 mm.

The electrodes disclosed herein may be ring electrodes, and/or printed electrodes on substrates (e.g., flexible circuit boards). Advantageously, printed electrodes may be spaced more closely than ring electrodes. In some embodiments, for example, printed electrodes spaced 0.1 mm apart have been successfully deployed in a planar array catheter. More typically, ring electrodes and printed electrodes have been advantageously spaced 0.5 mm to 4 mm apart. It has been found that such electrode spacing facilitates desirable electrophysiology mapping granularity in a number of cardiovascular applications, for example.

Short interelectrode spacing (e.g., 2 mm×2 mm) may be desirable to sample electrical characteristics of tissue (e.g., voltages) indicative of ablation line gaps. In testing, embodiments of the present disclosure including short interelectrode spacings of the electrode array detected ablation line gaps via the sampling of low voltage paths between lesions only separated by a few millimeters. Prior art electrophysiology mapping arrays, which lack the high-density electrode array and OIS/OT algorithm-based electrogram signal processing of the present disclosure, are not capable of detecting such minute ablation line gaps.

Aspects of the present disclosure are directed toward planar array catheters and basket catheters for electrophysiology mapping. More specifically, many embodiments of the present disclosure utilize printed circuit boards (e.g., flexible printed circuit boards) to form the planar array arms and/or basket splines. Further, aspects of the present disclosure include a plurality of electrodes positioned along the planar array arms and/or basket splines. In such embodiments, the planar array arms and/or basket splines may have electrodes conductively coupled to the flexible circuit board(s) that at least partially comprise structures of the arms and/or splines. The resulting cliques (or groups) of independently addressable electrodes facilitate electrophysiology measurements of tissue, in contact with the electrodes, which are orientation independent. That is, measurements may be taken across bipole pairs of electrodes within each clique (with a known distance therebetween) to capture measurements in at least two orientations. In more advanced 3D electrogram analysis, electrophysiology measurements may be captured in all three orientations. In some embodiments, it may be desirable for the electrodes of a clique to be placed equidistant one another to facilitate enhanced electrogram fidelity. This equidistant positioning of electrodes on a flexible circuit board may be accomplished by existing circuit board assembly techniques (e.g., surface mount technology component placement systems, commonly referred to as "pick-and-place" machines and circuit board printing techniques).

Conventional mapping catheter designs employ bipole electrode configurations to detect, measure, and display electrical signals from the heart. However, such conventional mapping catheter designs may be prone to error associated with the orientation of the bipole electrode pairs relative to an electrical wavefront of the heart, and result in displayed signals and mapping results that may be orientation dependent, and may not actually reflect the true (or desired) tissue properties. To mitigate this risk, aspects of the present disclosure are directed to signal processing techniques which may sample a plurality of bipole electrode pair configurations, with varying orientations, to produce accurate electrophysiology mapping results. To facilitate such signal processing techniques, electrophysiology mapping catheters consistent with the present disclosure (e.g., linear, planar array, and basket) may utilize cliques of electrodes that maintain spacing throughout various tissue contact configurations.

Inventors of the present disclosure have discovered that certain bipole electrode pair arrangements, such as those aligned with an activation direction of the electrical signals within the heart, show large amplitude signals reflecting depolarization traveling through normal or near normal tissue in contact with the bipole electrodes. Other alignments of the bipole pairs, for example, where the bipole pairs are aligned perpendicular to an activation direction of the electrical signals, or near scar tissue, may show lower amplitude fractionated signals. Various aspects of the present disclosure are directed to OIS/OT-like signal processing algorithms which separate signal amplitude and signal directionality despite poorly controlled catheter-wavefront orientation of the planar array.

For example, a first bipole pair of electrodes in an example clique samples an electrical signal passing through the contact tissue in an x-orientation, and a second bipole pair of electrodes in the clique samples a second electrical signal passing through the contact tissue in a y-orientation. Signal processing circuitry may then be used to determine the true 2-dimensional electrical signal for that location. The two bipole pairs, though substantially in the same location and in contact with the same tissue volume, may sample different electrical characteristics of the tissue due to the directionality of the electrical activation wavefronts traveling through the heart. For example, the electrical activation wavefronts that typically emanate from a sinoatrial node, and atrioventricular node. However, interfering electrical signals may also emanate from one or more of the pulmonary veins (e.g., arithmetic foci in the pulmonary vein(s)).

Figure 1B:
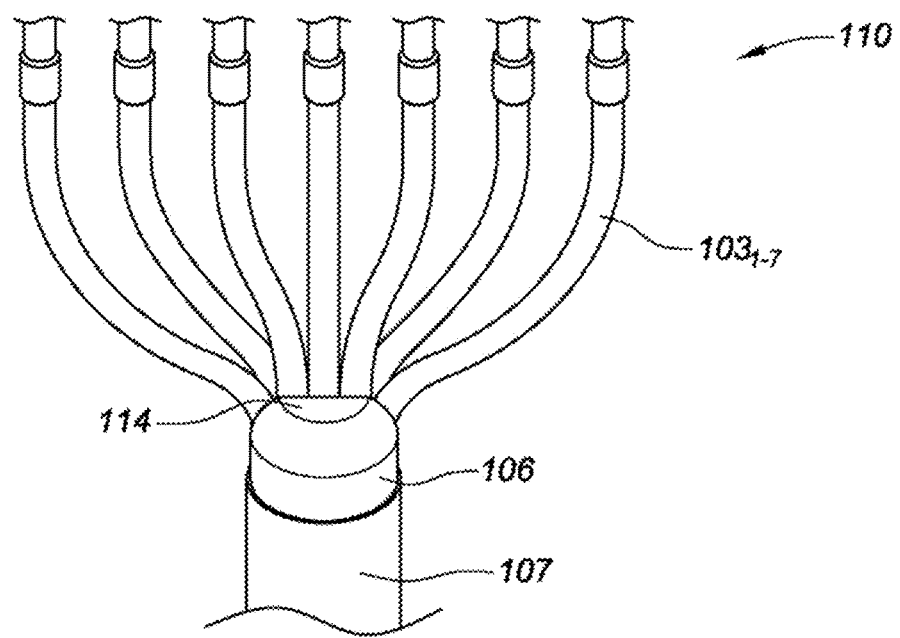
FIG. 1B is an enlarged, fragmentary view of a proximal portion of the planar array of FIG. 1A, consistent with various embodiments of the present disclosure.
Figure 1C:
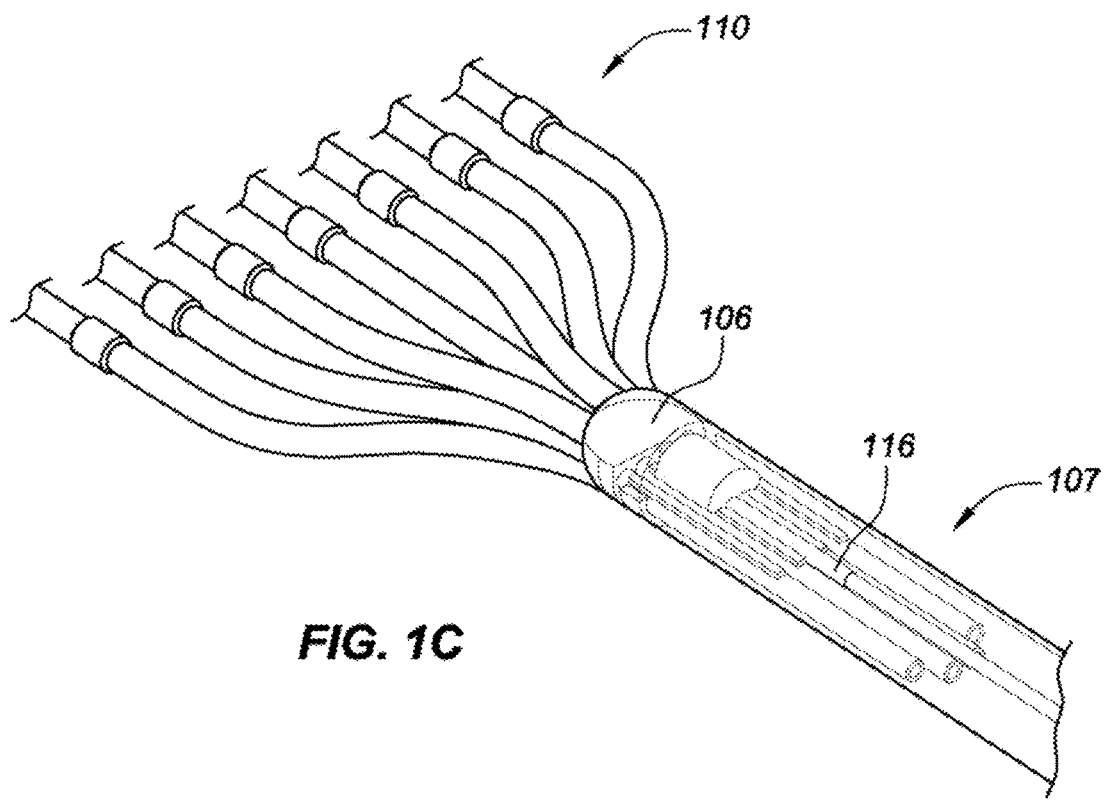
FIG. 1C is an isometric view of the planar array portion shown in FIG. 1B, consistent with various embodiments of the present disclosure.

Importantly, to facilitate determination of important electrical characteristics of the tissue (e.g., impedance), the distance between a first bipole pair and the distance between a second bipole pair must be known and constant. In FIGS. 1A-C, the spacing of electrodes $102_{1-N}$ on arms $103_{1-7}$ are precise and constant. Furthermore, in various embodiments it may be desirable for the distance between the two sets of bipole pairs for a clique to be the same.

The use of high-density electrode arrays, disclosed herein, facilitates the sampling of voltage measurements, for example, that are independent of effects associated with relative orientation of the catheter and electrical wavefront, making electrophysiology mapping of a cardiac muscle (and scar borders) much more reliable and precise. Moreover, embodiments of the present disclosure benefit from the collection of electrical signal timing information which is substantially independent from the electrode distribution. The high-density array of electrodes may also be used to verify sampled electrical signals from bipole pairs, by comparing the sampled electrical signal with other electrical signals sampled from adjacent (or nearby) bipole pairs. The regular spacing of electrodes in the high-density array further improves the accuracy of various metrics which are output from the OIS/OT algorithms and/or other signal processing techniques; for example, the En value (the estimate of the perpendicular bipole signal), an output of the Laplace equation, activation direction, conduction velocity, etc. Such aspects of the present disclosure are disclosed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, which are hereby incorporated by referenced as though fully disclosed herein.

Details of the various embodiments of the present disclosure are described below with specific reference to the figures.

FIG. 1A is a plan view of a planar array of an electrophysiology mapping catheter 101 including a high-density array of electrodes $102_{1-N}$, consistent with various embodiments of the present disclosure. The mapping catheter 101 includes a flexible tip portion 110 (also referred to as a planar array) that forms a flexible array of the electrodes $102_{1-N}$. This array of electrodes $102_{1-N}$ is coupled to a flexible framework of seven arms $103_{1-7}$ which extend in a plane that is substantially parallel with a longitudinal axis of catheter shall 107. Each of the arms is precisely, laterally separated from each other to facilitate exact spacing between electrodes $102_{1-N}$ on adjacent arms $103_{1-7}$, and the arms are coupled to one another at a distal and proximal end of the flexible tip portion 110 (e.g., at a distal tip 109 and bushing 106).

As shown in FIG. 1A, each of the seven arms $103_{1-7}$ may carry a plurality of electrodes 102, with the spacing between each electrode being the same (or at least known). Similarly, the spacing between electrodes 102 on adjacent arms 103 of the array may also be equal. As shown by way of example, electrodes within a bipole pair 104 have a center-to-center spacing of $D_A$, and electrodes within a bipole pair 104', that is oriented substantially orthogonal relative to bipole pair 104, have a center-to-center spacing of $D_B$, where $D_A$-$D_B$. For example, in some embodiments the center-to-center electrode spacing may be between 0.5-4 mm. In yet more specific embodiments, the center-to-center electrode spacing may be less than 0.5 millimeters (e.g. 0.1 mm). While the present embodiment is directed to electrode pairs with equal center-to-center spacing, various other embodiments of an electrode array consistent with the present disclosure may include an electrode array with equal edge-to-edge spacing. For example, in some embodiments the edge-to-edge electrode spacing may be between 0.5-4 mm. In yet more specific embodiments, the edge-to-edge electrode spacing may be less than 0.5 millimeters (e.g., 0.1 mm). Consideration of edge-to-edge spacing may be desirable where the electrodes of the array have different relative sizes (or surface areas).

Although the electrophysiology mapping catheter 101 in FIGS. 1A-C depicts seven arms, the catheters may comprise more or less arms, with spacing between each respective arm based on a desired electrode spacing for a given electrophysiology application. Additionally, while the electrophysiology mapping catheter 101 depicted in FIGS. 1A-C shows 56 electrodes (e.g., 8 electrodes 102 on each arm 103), the catheters may include, more or fewer than 56 electrodes, and each arm need not have the same number of electrodes as adjacent arms.

In some embodiments, the electrodes $102_{1-N}$ can be used in diagnostic, therapeutic, and/or mapping procedures. For example and without limitation, the electrodes 102 may be used for electrophysiological studies, pacing, cardiac mapping, and ablation, in some embodiments, the electrodes 102 can perform unipolar or bipolar ablation e.g., via the use of bipole pairs of electrodes 104 and 104'). This unipolar or bipolar ablation can create specific lines or patterns of lesions. In some embodiments, the electrodes 102 can receive electrical signals from the heart, which can be used for electrophysiological studies. Importantly, as the electrode spacing between adjacent electrodes on an arm 103, and those on adjacent arms, are the same, bipole pairs 104 and 104' with varying relative orientations may be sampled to determine electrical characteristics of the tissue in contact with the bipole pairs. The sampled electrical characteristics may be processed to remove catheter orientation-based signal effects. In some embodiments, the electrodes 102 can perform a location or position sensing function related to cardiac mapping; alternatively, ring electrodes 111 on a distal end of the catheter shaft 107 may be used to determine location and/or orientation of the catheter 101.

The flexible tip portion 110 of the catheter 101 is coupled to a distal end of a catheter shaft 107 at a bushing 106 (also referred to as a connector). The catheter shaft 107 may also define a catheter shaft longitudinal axis aa, as depicted in FIG. 1A. In the present embodiment, each of the arms 103 extend parallel to the longitudinal axis aa. The catheter shaft 107 may be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 may be used for diagnostic, therapeutic, localization and/or mapping procedures, for example.

The planar array 110 may be adapted to conform to tissue (e.g., cardiac tissue). For example, when the planar array 110 contacts tissue, each arm $103_{1-7}$ may independently deflect to conform to the tissue. The ability for the planar array to deflect in response to tissue may be particularly beneficial when the planar array comes into contact with contoured, irregular, or trabeculated tissue. In some embodiments, the arms (or the understructure of the arms) may be constructed from a flexible or spring-like material such as nitinol and/or a flexible substrate. The construction of the planar array arms $103_{1-7}$ (including, for example, the length and/or diameter of the arms, and material) may be adjusted or tailored to achieve desired resiliency, flexibility, foldability, conformability, and stiffness characteristics. Moreover, in some embodiments it may be desirable to vary one or more characteristics from the proximal end of an arm to the distal end of the arm, or between or among the plurality of arms forming the planar array 110. The foldability of materials such as nitinol and/or a flexible substrate provides the added benefit of facilitating insertion of the planar array into a delivery sheath or introducer, whether dining delivery of the catheter into the body or removal of the catheter from the body at the end of a procedure.

Planar array catheters including the high-density electrode array positioned thereon may be used for, for example: (1) defining regional propagation maps of particularly sized areas (e.g., one centimeter square areas) on the walls of the heart; (2) identifying complex fractionated atrial electrograms for ablation; (3) identifying localized, focal potentials between the microelectrodes for higher electrogram resolution; and/or (4) more precisely targeting areas for ablation. Electrophysiology mapping catheters, in accordance with the present disclosure, may be constructed to conform to, and remain in contact with, cardiac tissue despite potentially erratic cardiac motion. Such enhanced stability of the catheter on a heart wall during cardiac motion provides more accurate mapping due to sustained tissue-electrode contact. Additionally, the catheters described herein may find application in epicardial and/or endocardial use. For example, the planar array embodiments depicted herein may be used in epicardial procedures where the planar array of electrodes is positioned between the myocardial surface and the pericardium. Alternatively the planar array embodiments may be used in endocardial procedure to sweep and/or analyze the inner surfaces of the myocardium and create high-density maps of the heart tissue's electrical properties.

While various embodiments of the planar array 110 disclosed in the present disclosure are depicted with ring electrodes $102_{1-N}$ coupled to the arms $103_{1-7}$ (e.g., FIGS. 1A-C), embodiments with spot-type electrodes coupled to the arms are readily envisioned. Moreover, in yet further embodiments, the arms of the planar array may comprise flexible thin films compatible with printed circuit manufacturing techniques and/or have such thin films coupled to structural elements of the arm (e.g., nitinol-based arms). In such embodiments, spot-type electrodes may be printed onto the arms themselves. In flexible printed circuit embodiments of the present disclosure, the printed electrodes may be electrically coupled to signal processing circuitry and/or driver circuitry via traces extending on or within the one or more thin film layers. As many electrophysiology mapping applications require high signal fidelity, it is desirable to limit the transmission length of the analog signal, shield the transmission line itself, and/or convert the analog signal to a digital signal close to the source of the analog signal. Accordingly, aspects of the present disclosure are directed to placing signal processing circuitry (e.g., analog-to-digital converters, signal conditioning such as noise filtration and bandpass filters), and/or driver circuitry on the arms $103_{1-7}$ or in close proximity thereto.

In embodiments of the planar array including ring electrodes, the ring electrodes of the high-density electrode array may include the same type of electrode or a variety of various electrode types. For example, electrodes with smaller surface area may be used exclusively for electrophysiology mapping, while larger surface area electrodes may be used for mapping, tissue ablation, and/or localization. In some specific embodiments, a most-distal ring electrode 102 on a first outboard arm $103_1$ may be slightly enlarged as is the most-proximal ring electrode on a second outboard arm $103_7$. These slightly enlarged electrodes may be used, for example, for more precise localization of the flexible array in mapping and navigation systems. It may also be possible to drive ablation current between these enlarged electrodes, if desired, for bipolar ablation, or, alternatively to drive ablation current in unipolar mode between one or both of these enlarged ring electrodes and, for example, a patch electrode located on a patient (e.g., on the patient's back). Similarly, the electrodes $102_{1-N}$ in some embodiments may all be capable of performing unipolar or bipolar ablation therapies. Alternatively or concurrently, current could travel between one or more of the enlarged electrodes and any one or all of the electrodes. This unipolar or bipolar ablation therapy technique may be used to create specific lesion lines or lesion patterns. As also seen in FIG. 1A, there may be a distal member (or 'button') 109 where one or more of the arms $103_{1-7}$ come together. This distal member 109 may be constructed from metal or some other radiopaque material to provide fluoroscopy visualization. The distal member 109 may further facilitate (semi-)independent planar movement between the arms $103_{1-7}$.

FIG. 1B is an enlarged, fragmentary view of a proximal portion of the planar array 110 of FIG. 1A, consistent with various embodiments of the present disclosure, in some embodiments of the present disclosure, the planar array catheter may include one or more irrigant ports directed toward the planar array. For example, in FIG. 1B, a distal tip 109 of the catheter shaft 107 may be fitted with one or more irrigant ports directed toward the arms $103_{1-4}$ of the array. The bushing 106 at the distal end of the catheter shaft 107 couples each of the arms 103 to the catheter shaft 107. In yet more specific embodiments, one or more of the arms 103 may include fluid lumens that extend to irrigant ports positioned along a length of one or more arms, and/or may extend to a distal tip 109 (as shown in FIG. 1A) where one or more irrigant ports are directed distally toward the planar array 110.

FIG. 1C is an isometric view of the planar array portion 110 shown in FIG. 1B with hidden lines showing a distal portion of the catheter shaft 107. As shown in FIG. 1C, a sensor 116 (e.g., an impedance-based location sensor, a magnetic-based location sensor, etc) is mounted within/on the catheter shaft proximal to a bushing 106. A variety of sensors may be implemented at this location, or at other locations, of the various high-density mapping catheters described herein. These sensors 116 may be mounted in the catheter shaft 107, as shown in FIG. 1C, or may be mounted at other locations (e.g., along the electrode carrying arms $103_{1-7}$ of the high-density electrophysiology mapping catheter and/or at the distal tip 109. In some specific embodiments, the planar array may include two or more sensors positioned on or about the planar array to facilitate improved position and orientation identification of the planar array within a patient. In one embodiment, the sensor 116 is a magnetic field sensor configured for use with an electromagnetic localization system such as the Medi-Guide™ System sold by St. Jude Medical, Inc. of St. Paul, Minnesota.

Figure 2:
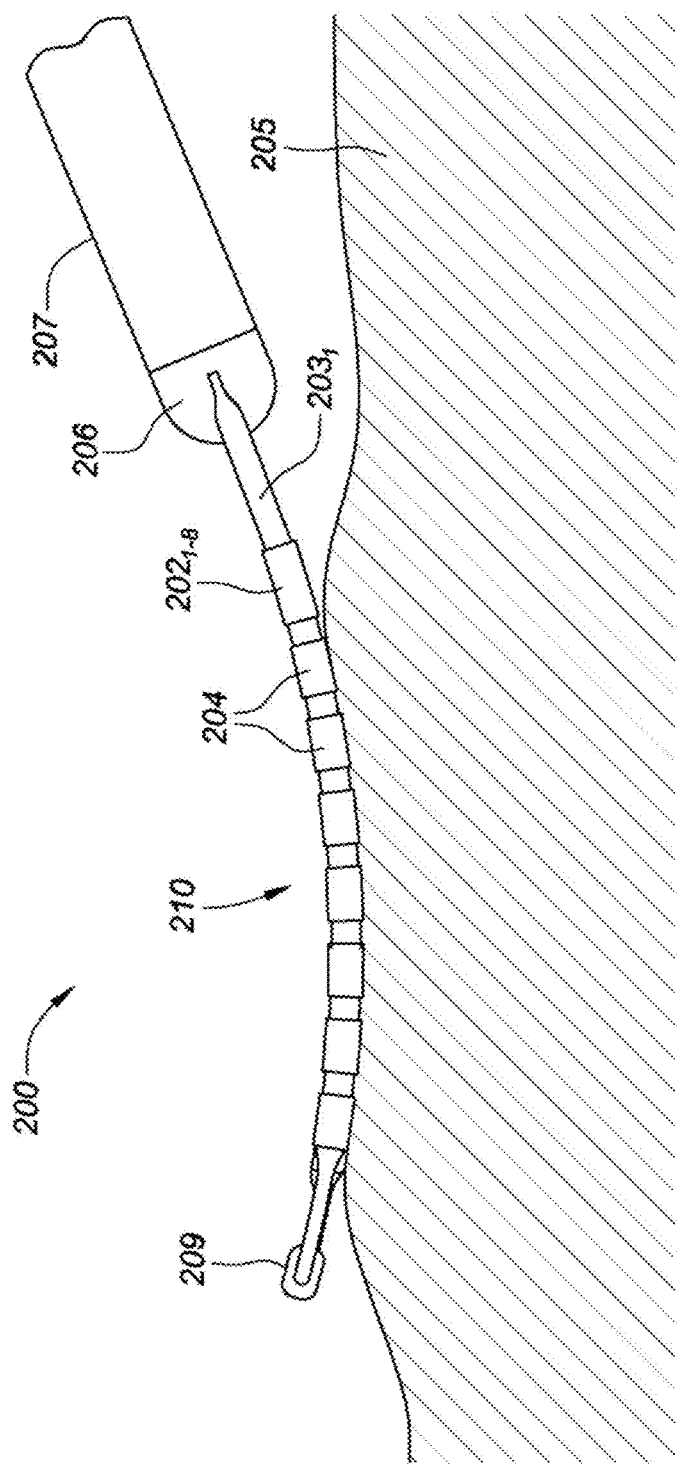
FIG. 2 depicts the planar array catheter shown in FIGS. 1A-C with the array of electrodes contacting tissue; consistent with various embodiments of the present disclosure.

FIG. 2 depicts a planar array catheter 200 including an array 210 of electrodes $202_{1-8}$ contacting tissue 205. The tissue 205 in the present embodiment is depicted as trabeculated, irregular, or contoured tissue. As shown in FIG. 2, the flexible arms of the planar array, including flexible arm $203_1$, conforms to the tissue 205, enabling a physician to place the planar array 210 (and its electrodes $202_{1-8}$) into constant contact with the tissue 205. As a result, the electrical signals (indicative of the tissue's electrical activity) sampled by the planar array exhibit enhanced accuracy, and thereby have improved diagnostic value. Each of the flexible arms $203_1$ include a plurality of electrodes $202_{1-8}$ which form cliques 204, and are coupled to the other adjacent arms of the planar array 210 at distal member 209 and bushing 206. The bushing 206 further couples the planar array 210 to shaft 207.

Figure 3:
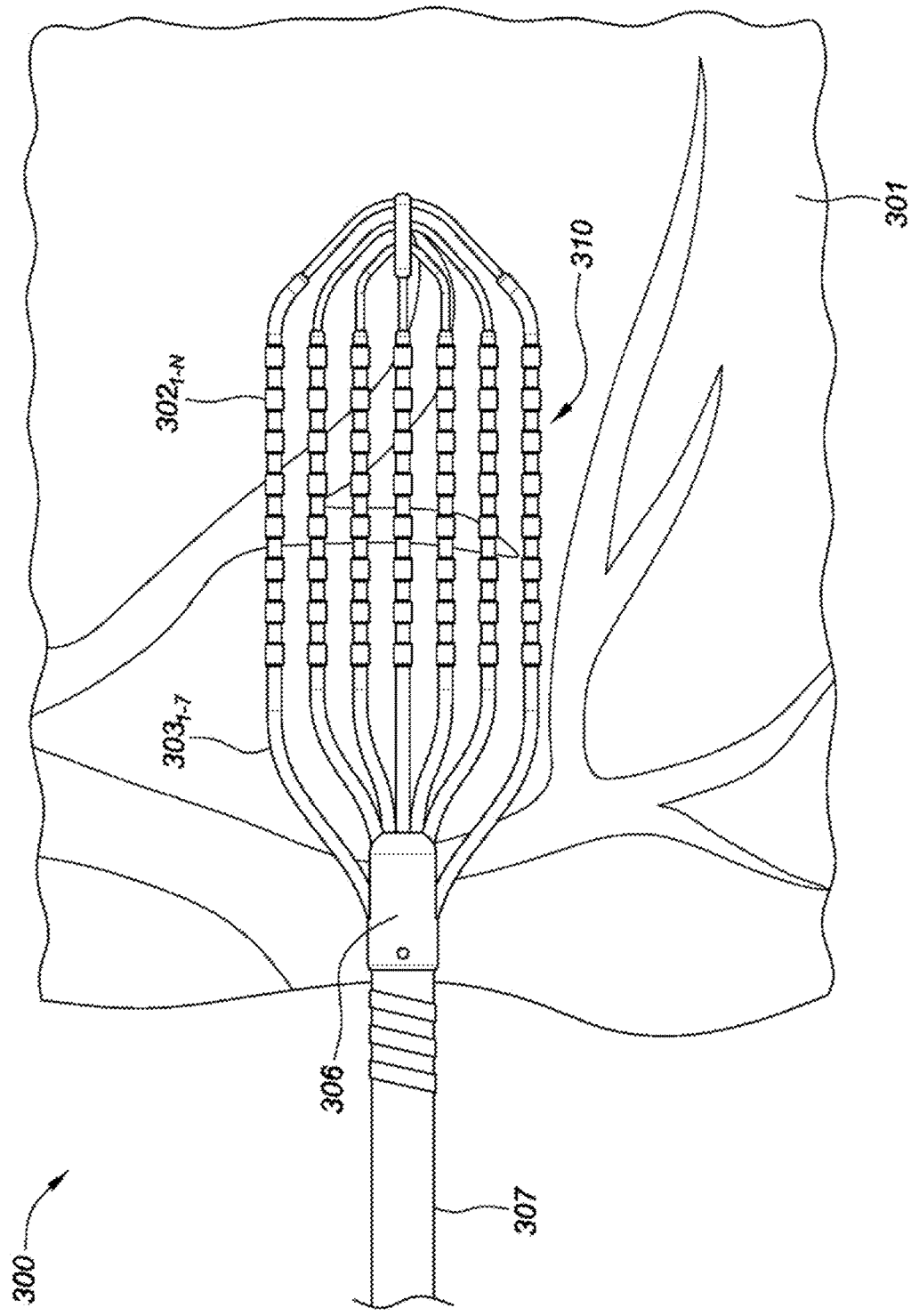
FIG. 3 depicts the planar array of the high-density mapping catheter of FIGS. 1A-C overlaying vasculature, consistent with various embodiments of the present disclosure.

FIG. 3 depicts a high-density mapping catheter 300 overlaying vasculature 301. In some embodiments of the present disclosure, the catheter 300 may include steering wires which extend a length of catheter shaft 307. Prior to reaching a bushing 306 that couples the catheter shaft 307 to arms $303_{1-7}$ of planar array 310, the steering wires may be coupled to steering rings which receive a tension from a proximal end of the steering wires and facilitates steering the catheter shall 307 and the planar array 310 through a patient's vasculature. As further shown in FIG. 3, each of the arms $303_{1-7}$ includes a plurality of electrodes $302_{1-N}$ distributed along a length of the arms. In the present embodiment, each of the electrodes are equally spaced from each of its adjacent electrodes. When controller circuitry samples electrical signals from bipole pairs of electrodes within the planar array 310, each of the bipole pairs will detect various electrical characteristics indicative of the tissue health in contact with the electrodes. The seven arms $303_{1-7}$ are designed to maintain the electrodes $302_{1-N}$ in a spaced relationship so that each electrode captures electrophysiology data of tissue at a known location relative to the other electrodes in the array.

Figure 4B:
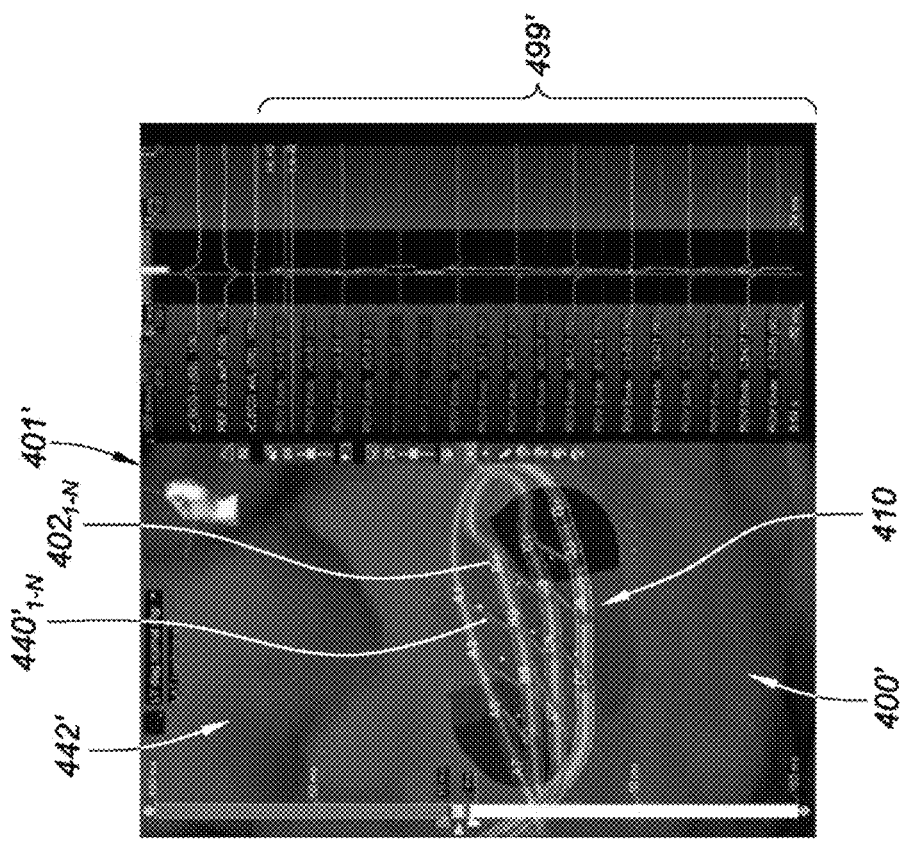
FIG. 4B depicts an electrophysiology mapping interface, consistent with various embodiments of the present disclosure.
Figure 4A:
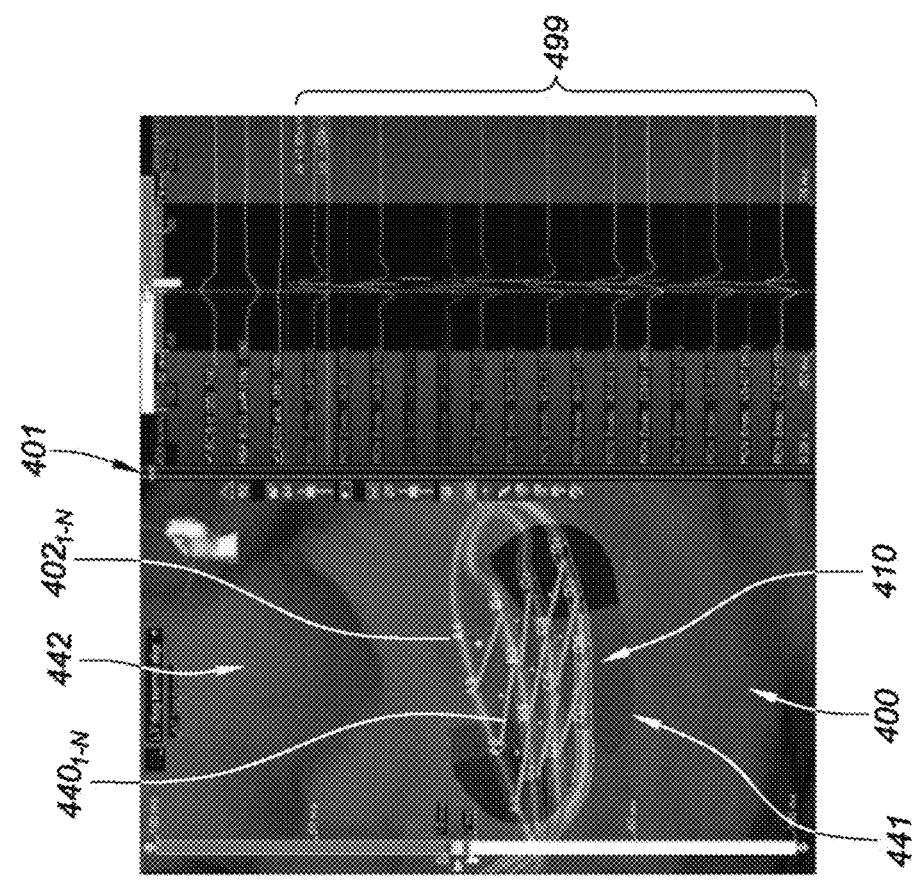
FIG. 4A depicts an electrophysiology mapping interface, consistent with various embodiments of the present disclosure.

FIG. 4A depicts an electrophysiology mapping interface 401, consistent with various embodiments of the present disclosure. The electrophysiology mapping interface 401 includes a plurality of real-time electrophysiology data streams 499 from various bipole pairs of electrodes across a planar array. A planar array visualization portion 400 of the interface 401 presents a representation of the planar array 410. The representation of the planar array 410 may utilize localization data to orient and position the planar array within a rendering of the cardiac muscle for example. Moreover, portions of the planar array in contact with tissue may be visually indicated in the planar array visualization 400. The green lines extending between electrodes $402_{1-N}$ on adjacent arms of the planar array 410 are indicative of a first configuration of bipole electrode pairs $440_{1-N}$. The electrical signals measured by the bipole pairs $440_{1-N}$ presented in the real-time electrophysiology data streams 499. In the present embodiment, the electrical activation direction within the tissue in contact with the planar array 410 extends from a left-side of the visualization to the right-side. Accordingly, the bipole pairs 440$_{1-N}$ are substantially aligned with the activation direction, resulting in electrogram data 499 from the bipole pairs 440$_{1-N}$ with relatively high amplitudes. This data is indicative of the true electrical characteristics of the tissue in contact with the planar array 410.

Upon receiving and processing electrogram data from the various bipole pairs of electrodes, the visualization 400 may be updated to color-code 441 a surface of the cardiac muscle model displayed in the visualization (often referred to as an electrophysiology map). The electrophysiology map may facilitate diagnosis by a clinician. For example, the clinician may use the mapped electrophysiology data to diagnose a cardiac arrhythmia (e.g., atrial fibrillation). To enable relative placement of the color-coded data 441 on the cardiac muscle model 442 in the visualization, controller circuitry associates the electrogram data from each bipole pair 440$_{1-N}$ with a location the data was collected. Determination of the planar array's position within a cardiac muscle may be facilitated by an impedance-based, electromagnetic, and/or hybrid localization system.

FIG. 4B depicts an electrophysiology mapping interface 401', consistent with various embodiments of the present disclosure. The electrophysiology mapping interface 401' includes a plurality of real-time electrophysiology data streams 499' from various bipole pairs of electrodes 440'$_{1-N}$ across a planar array 410. A planar array visualization. 400' portion of the interface 401' presents a representation of the planar array 410. The representation of the planar array 410 may utilize localization data to orient and position the planar array within a rendering of the cardiac muscle 442', for example. Moreover, portions of the planar array 410 in contact with tissue may be visually indicated in the planar array visualization 400'. The red lines extending between electrodes 402$_{1-N}$ on adjacent arms of the planar array 410 are indicative of a second configuration of bipole electrode pairs 440'$_{1-N}$. The electrical signals measured by the second configuration of bipole pairs are presented in the real-time electrophysiology data streams 499'. The data streams for each of the bipole pairs are collected simultaneously. In the present embodiment, the electrical activation direction within the tissue in contact with the planar array 410 extends from a left-side of the visualization to the right-side. Accordingly, the bipole pairs 440'$_{1-N}$ extend substantially orthogonal to the activation direction, resulting in electrogram data from the bipole pairs 440'$_{1-N}$ with relatively low amplitudes. This data is not indicative of the true electrical characteristics (e.g., maximal bipole amplitude characteristics) of the tissue in contact with the bipole pairs.

Figure 5:
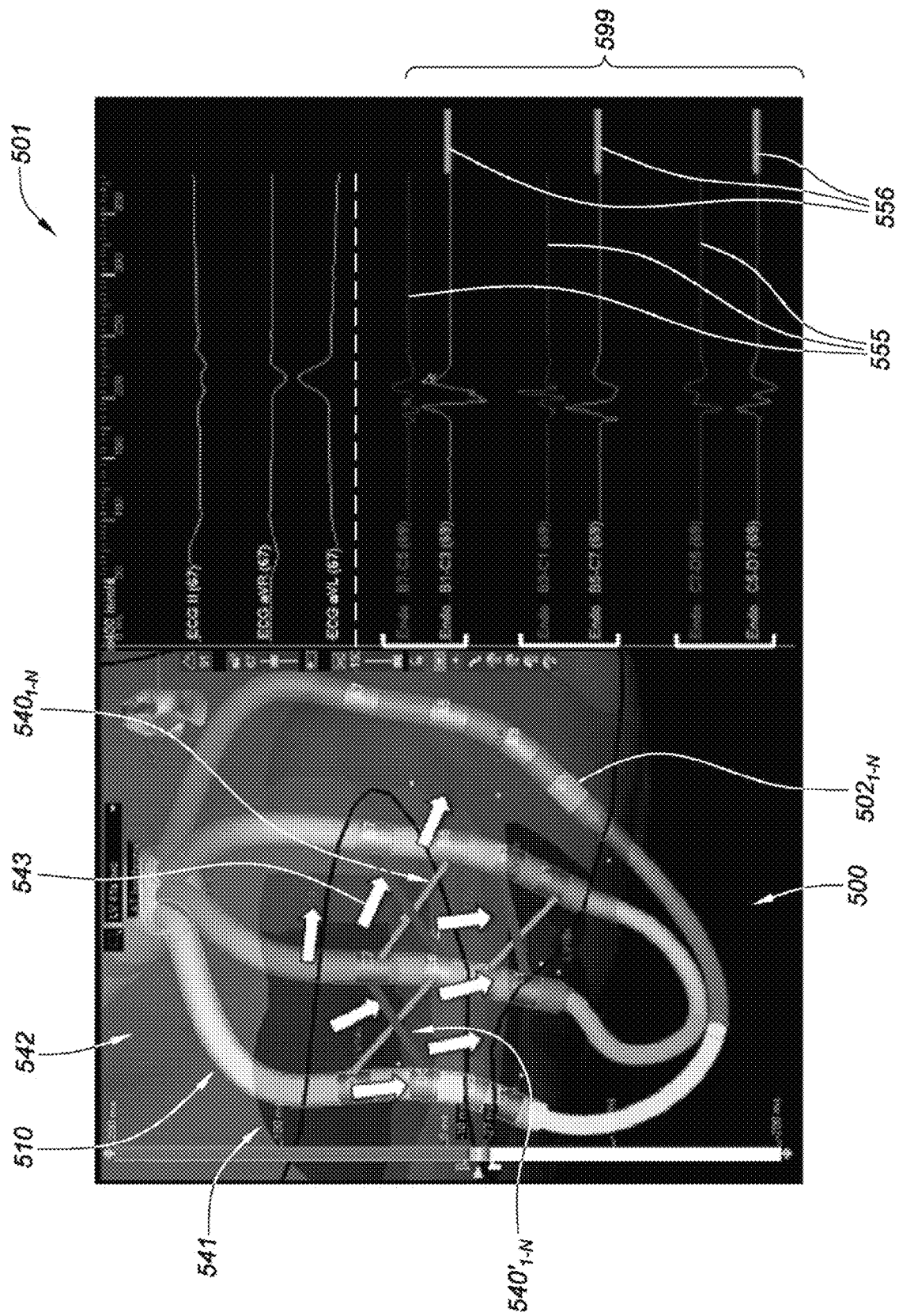
FIG. 5 depicts an electrophysiology mapping interface, consistent with various embodiments of the present disclosure.

FIG. 5 depicts an electrophysiology mapping interface 501, consistent with various embodiments of the present disclosure. The electrophysiology mapping interface 501 includes a plurality of real-time electrophysiology data streams 599 from various bipole pairs of electrodes across a planar array 510. A planar array visualization portion 500 of the interface 501 presents a representation of the planar array. As shown in FIG. 5, the representation of the planar array utilizes localization data to orient and position the planar array within a rendering of a cardiac muscle 542. The arrows are illustrative of an activation direction 543 of the electrical signals travelling through the cardiac muscle. The green lines extending between electrodes 502$_{1-N}$ on adjacent arms attic planar array 510 are illustrative of a first configuration of bipole electrode pairs 540$_{1-N}$. The electrical signals measured by the first configuration of bipole pairs 540$_{1-N}$ are presented as the green electrophysiology data streams 556.

The red lines extending between electrodes 502$_{1-N}$ on adjacent arms of the planar array are illustrative of a second configuration of bipole electrode pairs 540'$_{1-N}$. The electrical signals measured by the second configuration of bipole pairs 540'$_{1-N}$ are presented as the red electrophysiology data streams 555.

The electrophysiology data streams 556 of the first bipole pairs 540$_{1-N}$ show an increase in signal amplitude from the top left of the planar array 510 to the bottom right. The larger amplitude signals are indicative of depolarization traveling through normal or near normal myocardial tissue in contact with the bipole electrodes. Accordingly, the top-left of the planar array is color-coded 541 red to indicate less healthy tissue, with the more healthy tissue to the right and bottom of the screen being coded with greens and blues to indicate mare healthy tissue. The red coded tissue may be (near) scar tissue, for example, and may be a point of interest for clinicians.

The red electrophysiology data streams 555 show (fractionated) electrograms with low amplitude thresholds across the planar array 510. This is because the bipole pairs in the second configuration 540'$_{1-N}$ are aligned perpendicular to the activation direction 543 of the electrical signals. Due to the undesirable orientation, substantially orthogonal, between the second configuration of bipole pairs 540'$_{1-N}$ and the activation direction 543 of electrical signals through the cardiac muscle, the red electrophysiology data streams 555 do not represent the greatest possible local bipole voltage and thus may misrepresent a scar.

Figure 6:
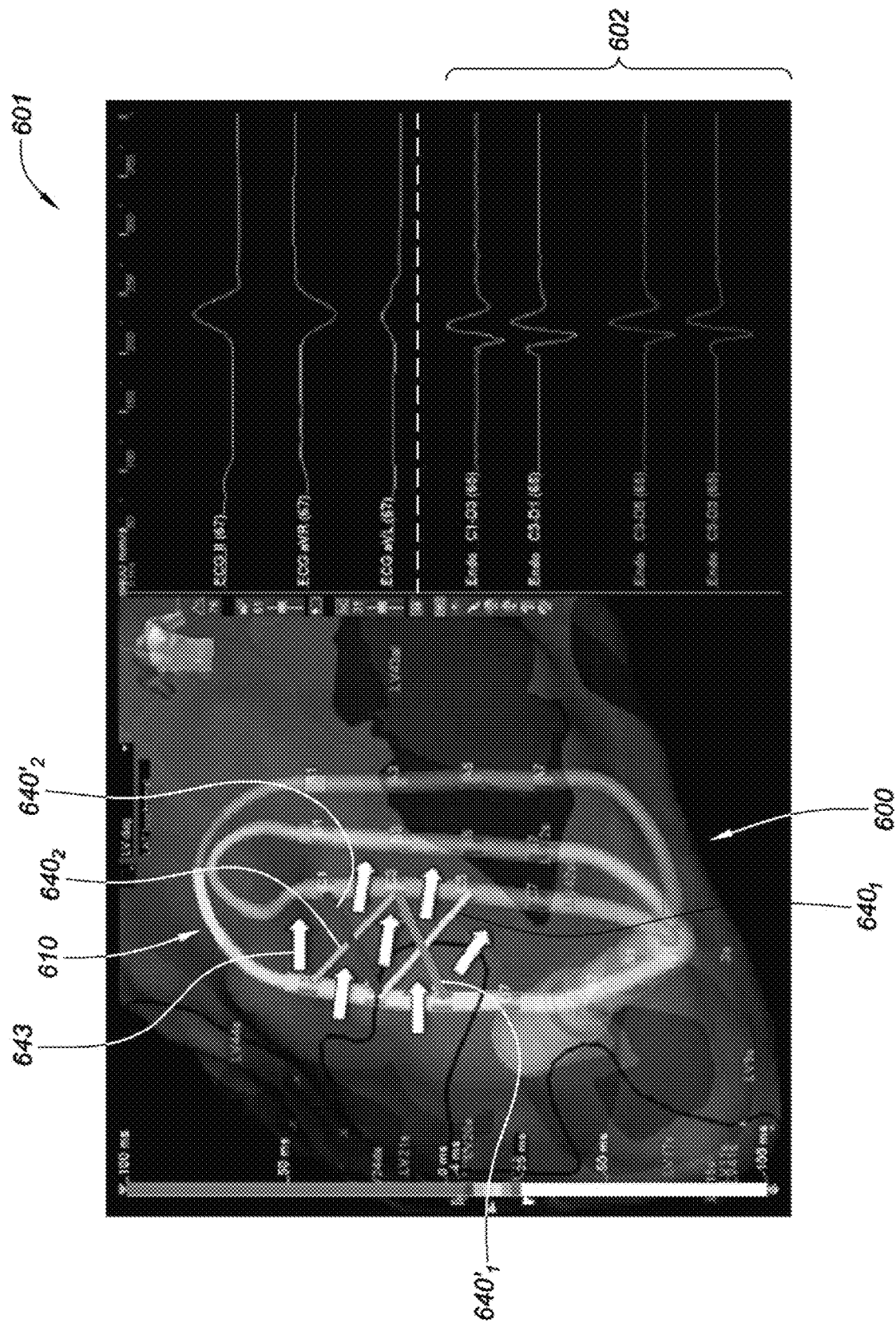
FIG. 6 depicts an electrophysiology mapping interface, consistent with various embodiments of the present disclosure.

FIG. 6 depicts an electrophysiology mapping interface 601, consistent with various embodiments of the present disclosure. Signal processing circuitry may utilize OIS/OT features, such as wave crest direction, to determine which fractionated electrograms 602 to ignore when developing an electrophysiology map 600 of a cardiac muscle. As a result, a clinician need not re-orient a planar array 610 on target tissue to verify that an electrogram signal is representative of the true activation signal traveling through the target tissue. Signal processing circuitry may further determine an activation direction 643 when the first and second configuration of bipole electrode pairs are both orientated approximately 45° from an activation direction 643. In such a case, the electrogram signals 602 from the first and second bipole electrode pairs (640$_{1-2}$ and 640'$_{1-2}$, respectively) of a target tissue will exhibit substantially the same signal. Both sets of signals exhibit similar local activity resolution and far field components.

Figure 7:
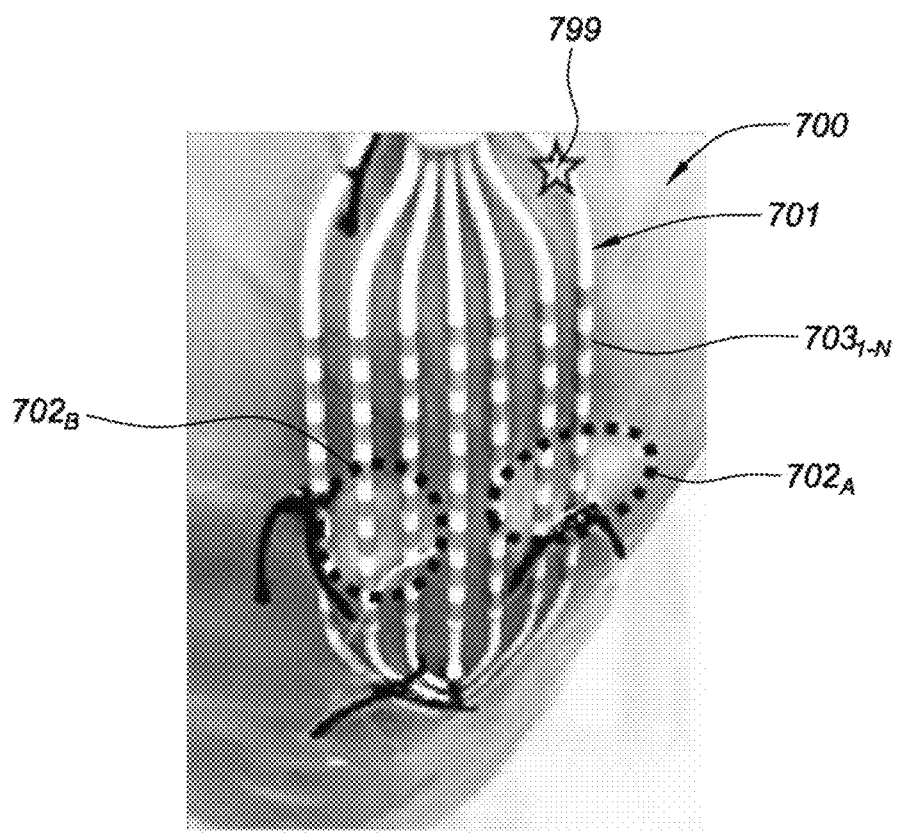
FIG. 7 depicts a planar array in contact with an epicardial layer of a cardiac muscle, consistent with various embodiments of the present disclosure.

FIG. 7 depicts a planar array 701 in contact with an epicardial layer of a cardiac muscle 700, consistent with various embodiments of the present disclosure.

FIG. 7 shows the cardiac muscle 700 after tissue ablation therapy has been conducted. The resulting ablation lesions 702$_{A-B}$ appear on the surface of the cardiac muscle 700 as white spots. To conduct an electrophysiology mapping of the cardiac muscle in proximity to the ablation locations, both before and after the ablation therapy, pacing is conducted from epicenter 799. Adjacent electrodes 703$_{1-N}$ are assigned to bipole pairings. During the pacing procedure, each bipole pair samples the electrical characteristics of the tissue in between the pair. The resulting electrical signals are received and processed by controller circuitry. The controller circuitry develops an electrophysiology mapping by associating the signal samples from each bipole pair with a location of the tissue sampled by the bipole pair. The electrogram from each bipole pair may be analyzed and various electrical characteristics may be visually indicated on an electrophysiology map by color-coding (or other visual indication scheme, e.g., shading, patterning, etc.). In some embodiments, the color-coding may be based on the electrogram voltage at each location (e.g., mean, average, max, etc.). In other embodiments, the number of times the electrical signal exceeds a threshold voltage (or a voltage slope changes signs) during a sampling window may be visually displayed on the map. In yet other embodiments, total energy sampled during a time window may be displayed. Various other methods of fractionation accounting are known and may be used as one or more factors of the resulting color-code displayed on the electrophysiology map.

FIG. 7A depicts the vertical, horizontal, and omnipole electrophysiology maps based on the electrical data collected from the planar array 710 of FIG. 7 before ablation of the contacted tissue. The vertical 705, horizontal 710, and omnipole 715 electrophysiology maps indicate that the tissue in contact with the planar array 710 is generally healthy. However, both the vertical 705 and horizontal 710 bipole maps evidence false-positive regions $704_{A-B}$ due to misaligned orientations of the activation direction of the electrical signals flowing through the cardiac muscle 700, and the bipole pairs' orientation. Specifically, as shown in FIG. 7, the activation direction emanates from epicenter 799, and moves down and to the left through the electrophysiology map shown in FIGS. 7A-B. As a result, both the vertical and horizontal electrophysiology maps 705 and 710 visually indicate moderately unhealthy tissue at the false-positive regions $704_{A-B}$. A positive tissue identification region may be defined by a low voltage signal that is actually indicative of completely ablated tissue. The omnipole electrophysiology map 715 is devoid of orientation-related false-positive regions, due to the controller circuitry sampling bipole pairs in each tissue region with substantially orthogonal orientation relative to one another. The controller circuitry may include signal processing circuitry which utilizes OIS/OT type algorithms to filter out low amplitude signals from bipole pairs that are misaligned with the activation direction of the pacing signal. Alternatively, the functionality of the OIS/OT type algorithms may be partially or completely conducted by a clinician manually. For example, a clinician may analyze an electrophysiology map using horizontal bipole pairs, followed by an analysis of a second electrophysiology map using vertical bipole pairs.

FIG. 7B depicts the vertical 705', horizontal 710', and omnipole 715' electrophysiology maps based on the electrical data collected from the planar array of FIG. 7, after ablation of the contacted tissue. While all three electrophysiology mapping methodologies identify the newly formed scar tissue at the ablation sites $702_{A-B}$ (due to the change in electrical activity caused by the necrosis of the tissue), the vertical 705' and horizontal 710' electrophysiology maps also detect false-positive regions $704_{C-D}$.

The false-positive region $704_C$ in the vertical map 705' is less severe than the false-positive region $704_D$ in the horizontal map 710' as the pacing source is positioned at the top-right of the map (see epicenter 799 in FIG. 7). Accordingly, activation direction of the pacing is substantially in-line with the vertical bipole pair arrangements in the vertical map 705', and orientated largely orthogonal to the horizontal bipole pairs sampled in the horizontal map 710'. As the omnipole map 715' looks at both vertical and horizontal bipole arrangements, these false-positive regions are largely eliminated providing a clinician with an electrophysiology map which more accurately depicts the true health of the tissue. For example, in an atrial fibrillation therapy, the clinician after analyzing the omnipole electrophysiology map 715' may determine that an additional spot ablation may be necessary between ablation sites $702_{A-B}$ to fully block the flow of stray electrical signals from one or more of the pulmonary veins in the left atrium.

As shown in FIG. 7B, the clinician, when looking at horizontal electrophysiology map 710' in isolation, may falsely establish the efficacy of the ablation therapy. The likelihood of such an event may be greatly increased where the activation direction is not otherwise known by the clinician (as opposed to a known pacing electrode position). In such a case, the clinician would need to rotate the planar array about the longitudinal axis in order to detect the false reading. However, such repositioning of the planar array may be limited by physical constraints within, for example, the left atrium of a cardiac muscle.

While various embodiments of high-density electrode catheters are disclosed herein, the teachings of the present disclosure may be readily applied to various other catheter embodiments as disclosed, for example, in the following patents and patent applications which are hereby incorporated by reference: U.S. provisional application No. 61/753,429, filed 16 Jan. 2013; U.S. provisional application No. 60/939,799, filed 23 May 2007; U.S. application Ser. No. 11/853,759 filed 11 Sep. 2007, now U.S. Pat. No. 8,187,267, issued 29 May 2012; U.S. provisional application No. 60/947,791, filed 3 Jul. 2007; U.S. application Ser. No. 12/167,736, filed 3 Jul. 2008, now U.S. Pat. No. 8,206,404, issued 26 Jun. 2012; U.S. application Ser. No. 12/667,338, filed 20 Jan. 2011 (371 date), published as U.S. patent application publication no. US 2011/0118582 A1; U.S. application Ser. No. 12/651,074, filed 31 Dec. 2009, published as U.S. patent application publication no. US 2010/0152731 A1; U.S. application Ser. No. 12/436,977, filed 7 May 2009, published as U.S. patent application publication no. US 2010/0286684 A1; U.S. application Ser. No. 12/723,110, filed 12 Mar. 2010 published as U.S. patent application publication no. US 2010/0174177; U.S. provisional application No. 61/355,242, filed 16 Jun. 2010; U.S. application Ser. No. 12/982,715, filed 30 Dec. 2010, published as U.S. patent application publication no. US 2011/0288392 A1: U.S. application Ser. No. 13/159,446, filed 14 Jun. 2011, published as U.S. patent application publication no. US 2011/0313417 A1; international application no. PCT/US2011/040629, filed 16 Jun. 2011, published as international publication no. WO 2011/159861 A2; U.S. application Ser. No. 13/162,392, filed 16 Jun. 2011 published as U.S. patent application publication no. US 2012/0010490 A1; U.S. application Ser. No. 13/704,619, filed 16 Dec. 2012, which is a national phase of international patent application no. PCT/US2011040781, filed 16 Jun. 2011, published as international publication no. WO 2011/159955 A1.

While various embodiments of the present disclosure are directed to the use of high-density electrode catheters in conjunction with OIS/OT algorithms, the teachings of the present disclosure may be readily applied to various other algorithm types. For example, embodiments consistent with the present disclosure may utilize the electrode signal post-processing techniques, and electrophysiology mapping algorithms disclosed in the following publications, which are hereby incorporated by reference: Magtibay et al. JAHA 2017 (J Am Heart Assoc. 2017; 6:e006447, DOI: 10.1161/JAHA.117.006447) (see, e.g., pages 6 and 7, and section titled "Omnipoles Provide the Largest Possible Bipolar Voltages"); and Haldar et al. Circulation AE 2017 (Circ Arrhythm Electrophysiol. 2017; 10:e005018.DOI: 10.1161/CIRCEP.117.005018) (see, e.g., page 6, section titled "Omnipolar Voltage Amplitude Correlates to Largest Measurable Bipolar Vpp," and FIG. 4).

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A planar array catheter comprising:
   an elongated catheter shaft defining a catheter longitudinal axis extending between a proximal end and a distal end; and
   a flexible, planar array at the distal end of the catheter shaft, the planar array configured to conform to tissue, and including two or more arms extending substantially parallel with the longitudinal axis and lying in a common plane, each of the arms having a plurality of electrodes mounted thereon;
   wherein the plurality of electrodes are configured to:
      detect an electrophysiological characteristic of tissue in contact with the planar array;
      output signals indicative of the detected electrophysiological characteristic of the tissue; and
      selectively ablate the tissue based at least in part on the detected electrophysiological characteristic of the tissue,
      wherein the plurality of electrodes are equally spaced along both a length of each arm and across adjacent arms.

2. The planar array catheter of claim 1, wherein the plurality of electrodes are further configured to selectively ablate the tissue using unipolar ablation.

3. The planar array catheter of claim 1, wherein the plurality of electrodes are further configured to selectively ablate the tissue using bipolar ablation.

4. The planar array catheter of claim 1, wherein three or more electrodes of the plurality of electrodes form a clique, the clique configured to sample electrical characteristics of a particular point of the contacted tissue in at least two substantially transverse directions, and the sampled electrical characteristics in at least one of the at least two substantially transverse directions are independent of the orientation of the planar array catheter relative to the tissue and thereby indicative of true electrical characteristics of the particular point of the contacted tissue.

5. The planar array catheter of claim 4, wherein the clique of the plurality of electrodes includes two or more bipole electrode pairs that extend diagonally across adjacent arms of the planar array.

6. The planar array catheter of claim 4, wherein the clique of the plurality of electrodes includes two or more bipole electrode pairs that extend along an arm of the planar array and across the arm and an adjacent arm of the planar array.

7. The planar array catheter of claim 1, wherein the plurality of electrodes include:
   a first plurality of electrodes configured to detect the electrophysiological characteristics of the tissue; and
   a second plurality of electrodes with a larger surface area compared to the first plurality of electrodes, the second plurality of electrodes configured to perform at least one of the following: detect the electrophysiological characteristics of the tissue, conduct selective tissue ablation, and conduct localization.

8. The planar array catheter of claim 1, wherein the center-to-center distance between adjacent electrodes of the plurality of electrodes is between 0.1 and 4 millimeters.

9. An electrophysiology system comprising:
   a planar array catheter including;
      a catheter shaft;
      a flexible, planar array coupled to a distal end of the catheter shaft, the planar array configured to conform to tissue, and including two or more arms extending substantially parallel with the longitudinal axis and lying in a common plane, each of the arms having a plurality of electrodes mounted thereon, the plurality of electrodes equally spaced along a length of each arm and across adjacent arms and configured to sample electrical characteristics of the contacted tissue; and controller circuitry communicatively coupled to each of the plurality of electrodes and configured to:
  sample electrical signals from each of the plurality of electrodes indicative of the electrical characteristics of the tissue in close proximity to each of the respective electrodes;
  process the sampled electrical signals to determine electrophysiological characteristics of the tissue; and
  selectively ablate the tissue based at least in part on the detected electrophysiological characteristics of the tissue.

10. The electrophysiology system of claim 9, wherein the controller circuitry is further configured to process the sampled electrical signals by determining true electrical characteristics of the contacted tissue independent of the orientation of the planar array catheter relative to the contacted tissue.

11. The electrophysiology system of claim 9, wherein the controller circuitry is further configured to:
  identify a clique of adjacent electrodes of the plurality of electrode including first and second bipole electrode pairs that extend substantially orthogonal relative to one another across the target tissue; and
  sample electrical characteristics of the tissue across the first and second bipole electrode pairs;
wherein the processing of the sampled electrical signals further includes associating the sampled electrical characteristics of the tissue across one of the first and second bipole electrode pairs with true electrical characteristics of the particular point of the contacted tissue.

12. The electrophysiology system of claim 11 wherein the controller circuitry is further configured to process the sampled electrical characteristics from the first and the second set of bipole electrodes through an OIS/OT algorithm, and to determine true electrical characteristics of the contacted tissue independent of the orientation of the first and second set of bipole electrodes relative to the contacted tissue.

13. The electrophysiology system of claim 9, wherein the planar array includes bipole electrode pairs that extend diagonally across adjacent arms of the planar array.

14. The electrophysiology system of claim 9, wherein the center-to-center distance between adjacent electrodes of the plurality of electrodes is between 0.1 and 4 millimeters.

15. The electrophysiology system of claim 9, further including a display communicatively coupled to the controller circuitry and configured to display at least one of an electrophysiology map or electrical signal indicative of one or more electrical characteristics of the contacted tissue, wherein the one or more electrical signals are independent of the orientation of the planar array catheter relative to the contacted tissue.

* * * * *